United States Patent
Lin

(10) Patent No.: US 11,630,105 B2
(45) Date of Patent: Apr. 18, 2023

(54) METHODS OF USING SELF-HEATING BIOSENSOR BASED ON LOSSY MODE RESONANCE

(71) Applicant: MING CHUAN UNIVERSITY, Taipei (TW)

(72) Inventor: Yu-Cheng Lin, Taipei (TW)

(73) Assignee: MING CHUAN UNIVERSITY, Taipei (TW)

( * ) Notice: Subject to any disclaimer, the term of this patent is extended or adjusted under 35 U.S.C. 154(b) by 0 days.

(21) Appl. No.: 17/736,666

(22) Filed: May 4, 2022

(65) Prior Publication Data
US 2022/0260560 A1 Aug. 18, 2022

Related U.S. Application Data

(62) Division of application No. 16/706,944, filed on Dec. 9, 2019, now abandoned.

(51) Int. Cl.
*G01N 33/543* (2006.01)
*G01N 21/552* (2014.01)
(Continued)

(52) U.S. Cl.
CPC ... *G01N 33/54373* (2013.01); *G01N 21/0332* (2013.01); *G01N 21/553* (2013.01); *G01N 21/7703* (2013.01)

(58) Field of Classification Search
CPC ......... G01N 33/54373; G01N 21/0332; G01N 21/553; G01N 21/7703
See application file for complete search history.

(56) References Cited

U.S. PATENT DOCUMENTS

| | | | | |
|---|---|---|---|---|
| 2004/0046963 A1* | 3/2004 | Lackritz | ............... | G01N 21/553 356/445 |
| 2006/0197960 A1* | 9/2006 | Bazylenko | ........... | G01N 21/253 356/491 |
| 2018/0275053 A1* | 9/2018 | Obara | ...................... | G01N 1/38 |

FOREIGN PATENT DOCUMENTS

WO WO-2014132717 A1 * 9/2014 ........... G01N 21/553

OTHER PUBLICATIONS

P. Zubiate, C. R. Zamarreno, P. Sanchez, I. R. Matias, and F. J. Arregu, "High sensitive and selective Creactive protein detection by means of lossy mode resonance based optical fiber devices," 2016, Biosensors and Bioelectronics, vol. 93, pp. 176-181 (Year: 2016).*

(Continued)

*Primary Examiner* — Samuel P Siefke
*Assistant Examiner* — Henry H Nguyen
(74) *Attorney, Agent, or Firm* — Chun-Ming Shih; HDLS IPR Services

(57) ABSTRACT

A self-heating biosensor based on lossy mode resonance (LMR) includes a waveguide unit and a lossy mode resonance layer. The waveguide unit is a flat plate, including two planes and at least two sets of opposite sides. One set of the opposite sides of the waveguide unit has a light input end and a light output end. The lossy mode resonance layer is disposed on one of the planes of the waveguide unit. Two heating electrodes are formed at two positions of the lossy mode resonance layer, and the two positions are relevant to one set of the opposite sides of the waveguide unit. A biomaterial sensing region having bioprobes are formed between the two heating electrodes. The present disclosure further includes a using method relevant to the self-heating biosensor based on lossy mode resonance.

1 Claim, 5 Drawing Sheets

(51) Int. Cl.
*G01N 21/77* (2006.01)
*G01N 21/03* (2006.01)

(56) References Cited

OTHER PUBLICATIONS

Cao et al., "Thermal tuning of graphene-embedded waveguide filters based on the polymer-silica hybrid structure", 2018, RSC Adv., 8, 30755-30760 (Year: 2018).*
Translation of WO2014132717A1, Kumazaki Nobutaka, Sep. 4, 2014 (Year: 2014).*
Kumar et al., "Glucose-and pH-Responsive Charge-Reversal Surfaces", 2014, Langmuir, 30, 16, 4540-4544. (Year: 2014).*

* cited by examiner

METHODS OF USING SELF-HEATING BIOSENSOR BASED ON LOSSY MODE RESONANCE

CROSS-REFERENCE TO RELATED APPLICATION

This application is a divisional application of U.S. patent application Ser. No. 16/706,944, filed on Dec. 9, 2019, and entitled "SELF-HEATING BIOSENSOR BASED ON LOSSY MODE RESONANCE AND, SENSING SYSTEM, METHODS OF USING THE SAME". The entire disclosures of the above application are all incorporated herein by reference.

BACKGROUND

Technical Field

The present disclosure relates to a biosensor, and more particularly to a biosensor based on the principle of lossy mode resonance (LMR) and having a self-heating function.

Description of Related Art

The statements in this section merely provide background information related to the present disclosure and do not necessarily constitute prior art.

In modern life, the life style of human beings changes with the development of the country and society. In the era of rapid technological development and convenient medical services, many countries have never developed into developing stage countries or developed stage countries, enjoying the convenience brought by technology is no longer a dream. The distance between countries is no longer a distance, no matter industry, information, culture, and food. But with the convenience of life and longevity, civilized diseases have also emerged, such as heart disease, cancer, obesity, and diabetes. Taking diabetes as an example, the main symptom is that the patient's blood sugar is higher than the standard value for a long time. Normally, when the body's blood sugar rises, it should be controlled by insulin to lower blood sugar. In the diabetes test, glycosylated hemoglobin (HbA1c) may be tested for the basis of blood glucose status for nearly 3 months.

In the past few years of bio-detection technology, surface plasmon resonance (SPR) technology has made great progress, and its high sensitivity makes it widely used in the biological and chemical fields for molecular grade detection. In many research works, the surface plasmon resonance (SPR) sensor is constructed by using a high refractive index prism with a metal layer on the surface. The angle of an incidence light has widely adjustable range. Therefore, any medium and the object to be tested may find a suitable angle to excite the surface plasma, and the incident light undergoes total internal reflection (TIR) at the interface between a waveguide and a resonance film and generates an evanescent wave. Wherein an incident light comprising a transverse electronic (TE) wave and transverse magnetic (TM) waves, surface plasmon resonance (SPR) technology may only excite the TM wave. As for selection for material of the metal layer, element of the surface plasma resonance generally has a better effect on a precious metal material such as gold or silver, but has the disadvantage that the material is expensive and easily oxidized. Furthermore, the sensor architecture using the prime-type design usually has a large volume, requires expensive optical equipment (such as lens group) and precision mechanical equipment (such as optical table systems), and is not easy to achieve miniaturization and mass production. Temperature has a great influence on biological reactions or chemical reactions. Moreover, stable temperature control is often required in outdoor environments, but current SPR or LMR components are not temperature controlled.

Therefore, how to design a biosensor to solve the technical problems above is an important subject studied by the inventors and proposed in the present disclosure.

SUMMARY

The purpose of the present disclosure is to provide a self-heating biosensor based on lossy mode resonance may achieve a purpose of low cost, miniaturization, and easy operation.

In order to achieve the purpose above-mentioned, the self-heating biosensor based on lossy mode resonance includes a waveguide unit, and a lossy mode resonance layer. The waveguide unit is a flat plate, including two planes and at least two sets of opposite sides, one set of the opposite sides of the waveguide unit has a light input end and a light output end. The lossy mode resonance layer is disposed on one of the planes of the waveguide unit, two heating electrodes are formed at two positions of the lossy mode resonance layer, and the two positions are relevant to one set of the opposite sides of the waveguide unit: a biomaterial sensing region having bioprobes formed between the two heating electrodes. Wherein the biomaterial sensing region is formed by performing a surface modification on the lossy mode resonance layer.

Another purpose of the present disclosure is to provide a self-heating biosensing system based on lossy mode resonance includes a broadband light source, an input optical fiber, a sensing module, an output optical fiber and a spectrometer. The input optical fiber coupled to the broadband light source. The sensing module coupled to the input optical fiber, and the sensing module includes a waveguide unit and a lossy mode resonance layer, the waveguide unit is a flat plate, including two planes and at least two sets of opposite sides, one set of the opposite sides of the waveguide unit has a light input end and a light output end, the lossy mode resonance layer is disposed on one of the planes of the waveguide unit, two heating electrodes are formed at two positions of the lossy mode resonance layer, and the two positions are relevant to one set of the opposite sides of the waveguide unit; a biomaterial sensing region having bioprobes are formed between the two heating electrodes. The output optical fiber coupled to the light output end. The spectrometer coupled to the output optical fiber. Wherein an incident light emitted by the broadband light source is configured to lossy mode resonance in the sensing module; and the biomaterial sensing region is formed by performing a surface modification on the lossy mode resonance layer.

Still another purpose of the present disclosure is to provide a method of using a self-heating biosensor based on lossy mode resonance, including the steps of: placing an object to be tested on a biological material sensing region with bioprobes of a lossy mode resonance layer; inputting an incident light from a broadband light source to a waveguide unit disposed under the lossy mode resonance layer; measuring a light output from the waveguide unit by a spectrometer; heating the biomaterial sensing region by energizing the lossy mode resonance layer.

When the foregoing self-heating biosensor based on lossy mode resonance is used, since the biomaterial sensing region is formed by a surface modification on the lossy mode resonance layer, so the biomaterial sensing region having the bioprobes are formed between two heating electrodes. When the bioprobes are composed of a boride functional group, the biomaterial sensing region may detect a glycated hemoglobin (HbA1c). In addition, the self-heating biosensor disclosed above is formed by disposing the lossy mode resonance layer on the waveguide unit, which is quite suitable for miniaturization. The waveguide unit may select a glass substrate which has low costs and small volume, and the lossy mode resonance layer may be selected as a resonance layer of lossy mode resonance (LMR) by using a light-transmissive metal oxide such as indium tin oxide (ITO) which with mature process and high yield coating technology (such as radio frequency (RF) magnetron sputter). The heating electrodes that formed at two positions of the lossy mode resonance layer may heat the biomaterial sensing region by applying an external voltage source, so that the operation of measuring the object to be tested is convenient. Therefore, the self-heating biosensor based on lossy mode resonance may achieve the purpose of low cost, miniaturization, and easy operation.

In addition, lossy mode resonance (LMR) has the following characteristics compare with surface plasma resonance (SPR): both TE wave and TM wave may resonate with the lossy mode resonance layer. However, SPR technology may only resonate with TM waves.

In order to further understand the techniques, means, and effects of the present disclosure for achieving the intended purpose. Please refer to the following detailed description and drawings of the present disclosure. The drawings are provided for reference and description only, and are not intended to limit the present disclosure.

DETAILED DESCRIPTION

Figure 1:
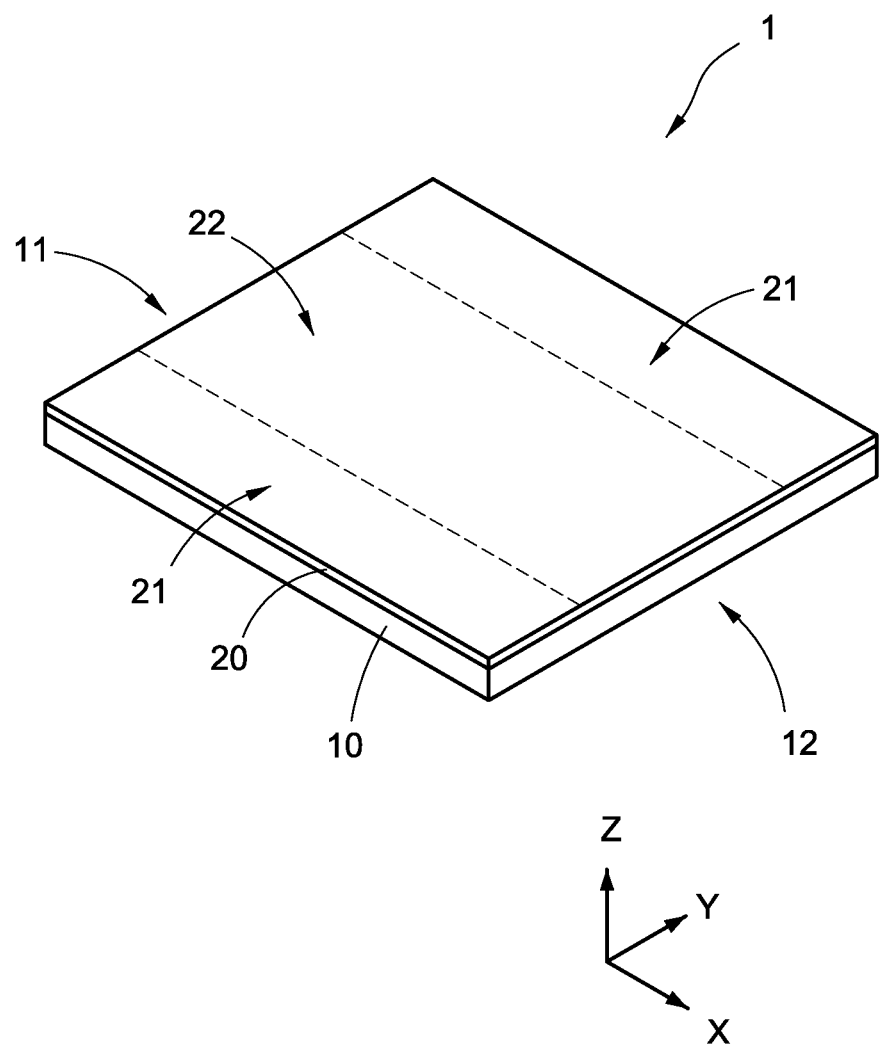
FIG. 1 is a schematic structural diagram of an embodiment of a self-heating biosensor based on lossy mode resonance.

The embodiments of the present disclosure are described by way of specific examples, and those skilled in the art may readily appreciate the other advantages and functions of the present disclosure. The present disclosure may be embodied or applied in various other specific embodiments, and various modifications and changes may be made without departing from the spirit and scope of the present disclosure.

It should be understood that the structures, the proportions, the sizes, the number of components, and the like in the drawings are only used to cope with the contents disclosed in the specification for understanding and reading by those skilled in the art, and it is not intended to limit the conditions that may be implemented in the present disclosure, and thus is not technically significant. Any modification of the structure, the change of the proportional relationship, or the adjustment of the size, should be within the scope of the technical contents disclosed by the present disclosure without affecting the effects and the achievable effects of the present disclosure.

The technical content and detailed description of the present disclosure will be described below in conjunction with the drawings.

Figure 2:
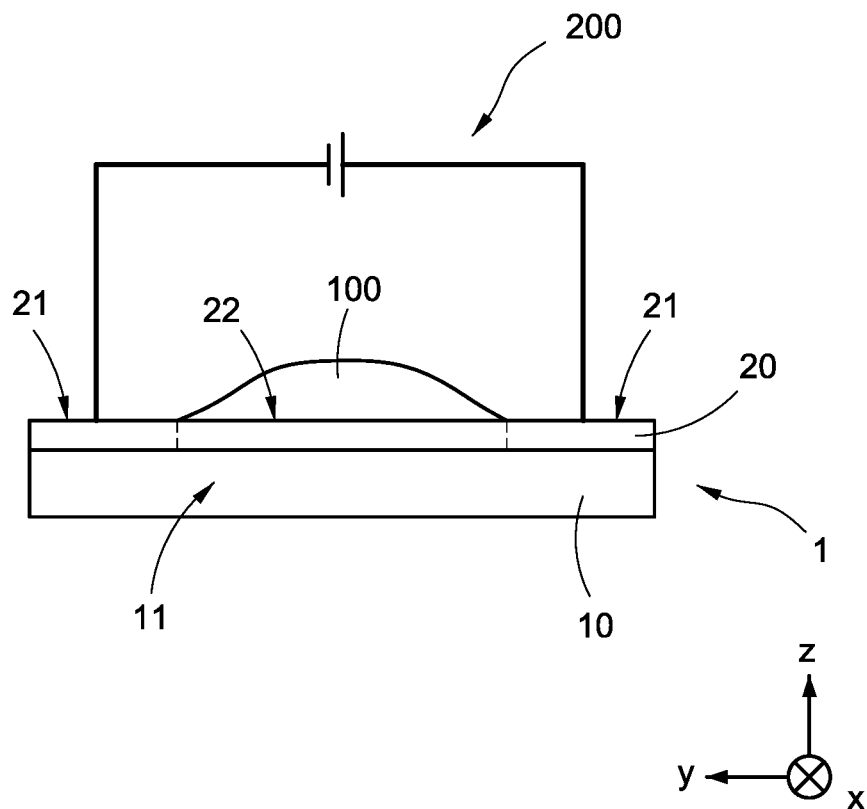
FIG. 2 is a schematic diagram of measuring an object to be tested by the self-heating biosensor based on lossy mode resonance.

Please refer to FIG. 1 and FIG. 2. FIG. 1 is a schematic structural diagram of an embodiment of a self-heating biosensor based on lossy mode resonance. FIG. 2 is a schematic diagram of measuring an object to be tested by the self-heating biosensor based on lossy mode resonance.

The self-heating biosensor 1 based on lossy mode resonance of the embodiment of the present disclosure includes a waveguide unit 10 and a lossy mode resonance layer 20.

The waveguide unit 10 is a quadrilateral flat plate, and includes two planes and two sets of opposite sides. One set of the opposite sides of the waveguide unit 10 are respectively a light input end 11 and a light output end 12. In the embodiment, the waveguide unit 10 may be one of a glass substrate, a quartz substrate, a photonic crystal substrate, and a polymer material substrate, or may be made of other materials having low light loss.

Although the optical fiber sensor is currently in the mainstream, a manufacturing process of the optical fiber sensor needs to be ground and coated, which is not easy to manufacture. Taking a plastic optical fiber (POF) as an example, although the toughness thereof is better, but it is difficult to resist the organic solution and high temperature in the process, and the wavelength range of the absorption spectrum of POF is between red light and infrared light. The absorption spectrum is a commonly used wavelength and is not easily used to determine SPR and LMR phenomena. Taking a glass optical fiber (GOF) as an example, although it may resist the organic solution and high temperature in the process, and the absorption spectrum is in ultraviolet light, and the ultraviolet light is not a commonly used wavelength, the GOF is not easy to grind and break. In summary, the present disclosure proposes to use a planar waveguide base on glass as a sensor, and the glass substrate is first coated and then cut to an appropriate size. Glass may resist the organic solution and high temperature in the process, and does not need to be ground. Compared with the optical fiber sensor, the planar waveguide makes the sensor easier, is not easy to damage, and has high yield.

The lossy mode resonance layer 20 is disposed on one of the planes of the waveguide unit 10, two heating electrodes 21 are formed at two positions of the lossy mode resonance layer 20, and a biomaterial sensing region 22 having bioprobes are formed between the two heating electrodes 21, wherein the two positions are relevant to one set of the opposite sides of the waveguide unit 10. The biomaterial sensing region 22 is formed by performing a surface modification on the lossy mode resonance layer 20. In the present embodiment, the bioprobe is composed of a boride functional group, and the lossy mode resonance layer 20 may be selected a metal oxide such that the real part of the dielectric constant is much larger than the imaginary part of the dielectric constant, there is an opportunity to generate a lossy mode. The lossy mode resonance layer 20 may be composed of a metal oxide (one of indium tin oxide (ITO), zinc oxide (ZnO), or titanium oxide (TiO2)) or a polymer material. The biomaterial sensing region 22 is used to set an object to be tested (or call a device under test, DUT). In the present embodiment, the object to be tested 100 may be a phosphate buffer solution (PBS) including glycated hemoglobin (HbA1c), as shown in FIG. 2. When the object to be tested 100 measuring, an external voltage source 200 may be applied to the two heating electrodes 21 to heat the biomaterial sensing region 22. In addition, the lossy mode resonance layer 20 may also form a DNA probe after surface modification, the DNA probe used to combine with complementary DNA, and the DNA probe may be released from the complementary DNA by heating the biomaterial sensing region 22.

The principle of LMR is similar to the principle of SPR. When an incident light enters the lossy mode resonance layer 20 at a critical angle and total internal reflection (TIR) occurs, the incident light generates an evanescent wave on the surface of the lossy mode resonance layer 20. When the evanescent wave is matched with the effective refractive index of the lossy mode resonance layer 20, they are coupled to observe the light intensity loss of the partial wavelength from a spectrum of reflected light. The wavelength with loss of light intensity is called an LMR wavelength and is a focus of observation in the present disclosure. In addition, both TE wave and TM wave may resonate with the lossy mode resonance layer 20, so there is no need to polarize or filter the incident light, and the sensitivity is high and the use is convenient.

In the present embodiment, the indium tin oxide layer as the lossy mode resonance layer 20 is disposed on the glass substrate as the waveguide unit 10 by RF magnetron sputter. RF magnetron sputter is well known and mature in the art and will not be described in detail herein. The surface modification is carried out sequentially in the following first to fourth steps. The first step is to remove surface contaminants of an indium tin oxide layer. The second step is to carry out a hydroxylate treatment to the indium tin oxide layer. The third step is to carry out a salinization treatment to the indium tin oxide layer. The fourth step is to carry out a decarboxylate treatment for the indium tin oxide layer. Details are as follows.

Figure 3:
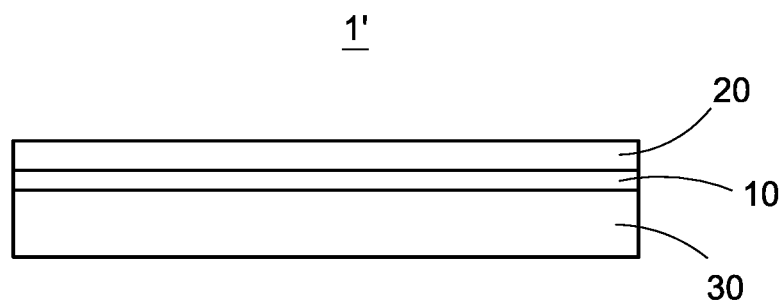
FIG. 3 is a schematic structural diagram of another embodiment of the self-heating biosensor based on lossy mode resonance.

Please refer to FIG. 3, which is a schematic structural diagram of another embodiment of the self-heating biosensor based on lossy mode resonance. The self-heating biosensor 1' is substantially the same as the self-heating biosensor 1 of the first embodiment of the present disclosure, except that the other surface of the waveguide unit 10 that without the lossy mode resonance layer 20 is disposed on a substrate 30. In this way, the amount of material of the waveguide unit 10 may be reduced, mechanical strength may be maintained at the same time, and the cost may be saved.

Figure 4:
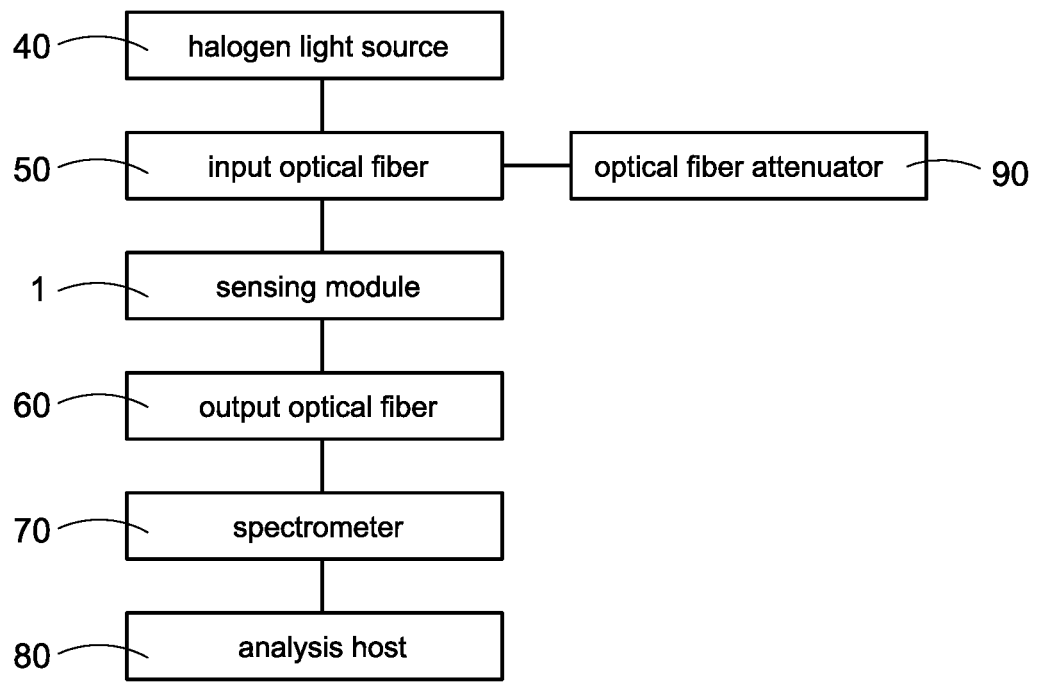
FIG. 4 is a functional block diagram of a self-heating biosensing system based on lossy mode resonance.
Figure 5:
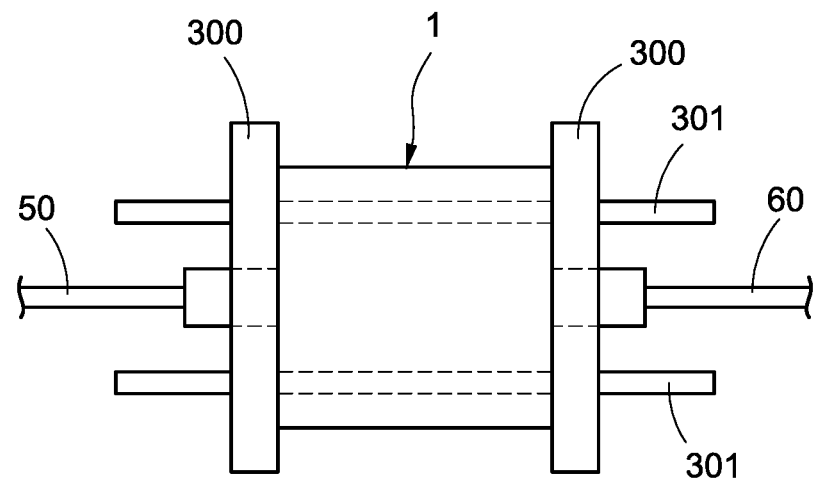
FIG. 5 is a schematic diagram of a jig for a fixed sensing module in the self-heating biosensing system based on lossy mode resonance.

Please refer to FIG. 4 and FIG. 5. FIG. 4 is a functional block diagram of a self-heating biosensing system based on lossy mode resonance. FIG. 5 is a schematic diagram of a fixture for a fixed sensing module in the self-heating biosensing system based on lossy mode resonance.

As shown in FIG. 4, when the self-heating biosensor 1 based on the lossy mode resonance is disposed in a system for measurement, the self-heating biosensor 1 as a sensing module coupling a broadband light source (such as the halogen light source 40 shown in the figure) by coupling an input optical fiber 50. The self-heating biosensor 1 is coupled to a spectrometer 70 by coupling an output optical fiber 60. Finally, the spectrometer 70 may be coupled to an analysis host 80 for analysis of measured values. An optical fiber attenuator 90 may be added to the input optical fiber 50, and the amount of light intensity attenuation may be manually adjusted. In this embodiment, the halogen light source 40 used may generate incident light having a wavelength range of 400 nm to 1800 nm. The wavelength range detectable by spectrometer 70 is suitable for the halogen light source 40. Referring to FIG. 2 and FIG. 4, when the self-heating biosensor 1 is used in the system, the object to be tested 100 is placed in the biomaterial sensing region 22, and an incident light emitted by the halogen light source 40 is input to glass substrate as the waveguide unit 10 by the light input end 11. A light (i.e., the light reflected from the lossy mode resonance layer 20) output from the light output end 12 of the glass substrate is measured by the spectrometer 70. Finally, by applying the external voltage source 200 to the two heating electrodes 21 of the indium tin oxide layer to heat the biomaterial sensing region 22, the DNA probe may release the complementary DNA. The heating electrodes 21 may also perform heating and temperature control for specific temperature requirements of different samples in measurement process.

As shown in FIG. 5, during the measurement process, a jig 300 may be disposed between the input optical fiber 50 and the output optical fiber 60, and a jig 300 may be used to fix the self-heating biosensor 1 to build a measurement platform. In the present embodiment, the jig 300 may be made of stainless steel and matched with an adjustable slide rail 301 to match different sizes of the self-heating biosensor 1 to make measurement and application more convenient. The measuring platform of this embodiment is applied to the input optical fiber 50 and the output optical fiber 60 of fiber connector (FC). When a thickness of the glass substrate is 0.7 mm, the center of the two sides of the fiber corresponds to the position of the glass at 0.35 mm (at the center of the glass substrate). In this way, the incident light may be efficiently collected, and even if the thickness of the glass substrate is increased, it may be incident into the glass substrate.

Figure 6:
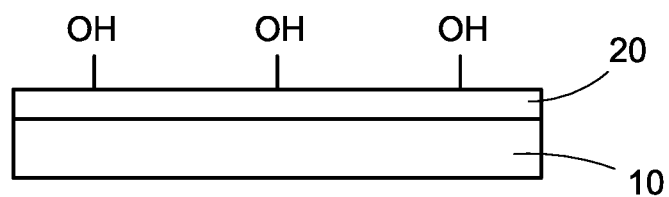
FIG. 6 to FIG. 8 are schematic diagrams showing a surface modification of the self-heating biosensor based on lossy mode resonance.
Figure 7:
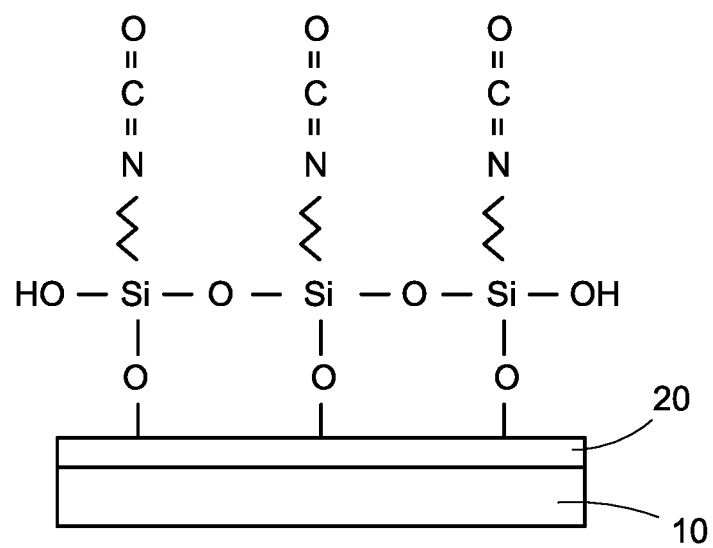
Figure 8:
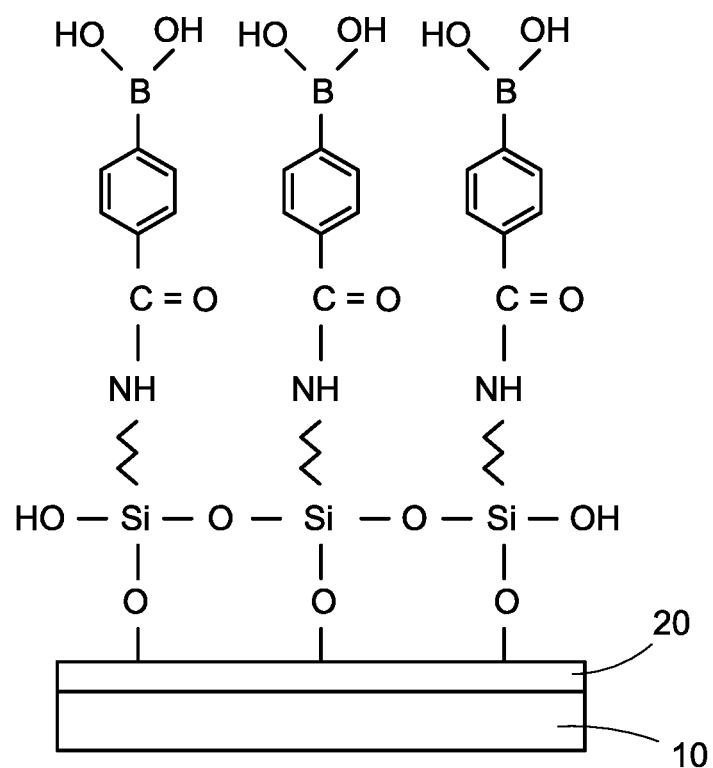

Please refer to FIG. 6 to FIG. 8. There are schematic diagrams showing a surface modification of the self-heating biosensor based on lossy mode resonance.

The indium tin oxide layer on the glass substrate itself cannot adsorb HbA1c, and indium tin oxide (ITO) must be bonded to the boride functional group through the surface modification, so let the boride functional group adsorbs HbA1c. The LMR wavelength is also displaced when the indium tin oxide layer is adsorbed to HbA1c, thereby achieving purpose for detection. The first step is cleaning, and the indium tin oxide layer as the lossy mode resonance layer 20 is sequentially washed with acetone, absolute ethanol, ultrapure water, potassium hydroxide aqueous solution, and ultrapure water. The second step is a hydroxylation treatment, and the lossy mode resonance layer 20 is washed with an RCA solution (i.e., a mixed solution of ammonia water and hydrogen peroxide) to remove organic contaminants and generate hydroxyl groups (OH), as shown in FIG. 6. The third step is the salinization treatment, the hydroxyl group is attached to the silane, leaving the end with isocyanate and boric acid combined, as shown in FIG. 7. The fourth step is a decarboxylation treatment to remove the carboxyl group (COOH) to facilitate the bonding of the isocyanate group to the benzene ring. As shown in FIG. 8, carbon dioxide is generated during the reaction, so that bubble generation may be observed. That is, the surface modification has been successful.

In research of the present disclosure, LabView and Mathscript are used to simulate LMR to cause TE wave and TM wave loss. There are four parameters in the program for the user to adjust, including: glass substrate thickness ($d_1$), ITO thickness (d2), the length of the sensing area (L) and the refractive index of the object to be tested (n3). There are two parameters that vary with the wavelength of the incident light, including: glass substrate refractive index (n1) and ITO refractive index (n2). The most obvious parameter affecting LMR sensitivity is ITO thickness (d2), which is one of the characteristics of LMR. SPR cannot improve the sensitivity of the sensor by the thickness of the resonance layer. According to the simulation results, in the case of L=30 mm and d1=30 mm, if the ITO thickness is thinner, the loss of LMR wavelength is increased, which is beneficial to signal extraction and sensitivity, and the transmittance is about −10dB to −20dB, the incident light intensity is different from the reflected light intensity by 10 to 100 times. Please refer to the following table:

| ITO thickness (nm) | 80 | 100 | 120 |
|---|---|---|---|
| Sensitivity ($\lambda$/RIU) | 1853 | 1506 | 1253 |
| Transmittance (dB) | −10.4~−21.5 | −12.6~−20.8 | −14.7~−21.2 |

When the foregoing self-heating biosensor 1 based on lossy mode resonance is used, since the biomaterial sensing region 22 is formed by the surface modification on the lossy mode resonance layer 20, so the biomaterial sensing region 22 having the boride functional group is formed between the two heating electrodes 21, and may be detected for HbA1c. In addition, the self-heating biosensor 1 disclosed above is formed by disposing the lossy mode resonance layer 20 on the waveguide unit 10, which is quite suitable for miniaturization. The waveguide unit may select a glass substrate which has low costs and small volume, and the lossy mode resonance layer 20 may be selected as a resonance layer of lossy mode resonance (LMR) by using a light-transmissive metal oxide such as ITO which with mature process and high yield coating technology (such as RF magnetron sputter). The heating electrodes 21 that formed at two positions of the lossy mode resonance layer 20 may heat the biomaterial sensing region 22 by applying an external voltage source 200, so that the operation of measuring the object to be tested 100 is convenient. Therefore, the self-heating biosensor 1 based on lossy mode resonance may achieve the purpose of low cost, miniaturization, and easy operation.

In addition, lossy mode resonance (LMR) has the following characteristics compare with surface plasma resonance (SPR): both TE wave and TM wave may resonate with the lossy mode resonance layer. However, SPR technology may only resonate with TM waves.

The above is only a detailed description and drawings of the preferred embodiments of the present disclosure, but the features of the present disclosure are not limited thereto, and are not intended to limit the present disclosure. All the scope of the present disclosure shall be subject to the scope of the following claims. The embodiments of the spirit of the present disclosure and its similar variations are intended to be included in the scope of the present disclosure. Any variation or modification that may be easily conceived by those skilled in the art in the field of the present disclosure may be covered by the following claims.

What is claimed is:

1. A method of using a self-heating biosensor based on lossy mode resonance, comprising the steps of:
   placing an object to be tested on a biological material sensing region with bioprobes of a lossy mode resonance layer,
   inputting an incident light from a broadband light source to a waveguide unit disposed under the lossy mode resonance layer,
   measuring a light outputted from the waveguide unit by a spectrometer, and
   heating the biomaterial sensing region by energizing the lossy mode resonance layer,
   wherein the bioprobes are consisting of a boride functional group, a formation of the boride functional group comprises:
   sequentially cleaning the lossy mode resonance layer with acetone, absolute ethanol, ultrapure water, potassium hydroxide aqueous solution, and ultrapure water;
   cleaning the lossy mode resonance layer with a mixed solution of ammonia water and hydrogen peroxide to remove organic contaminants and generate hydroxyl groups (OH) by a hydroxylation treatment;
   attaching the hydroxyl groups to a silane and leaving an end with isocyanate to be combined with boric acid by a salinization treatment;
   removing a carboxyl group (COON) to bond an isocyanate group to a benzene ring by a decarboxylation treatment;
   wherein carbon dioxide is generated by the lossy mode resonance layer during a reaction, bubbles generation is observed, and the boride functional group is formed.

* * * * *